United States Patent [19]
Mulye

[11] Patent Number: 6,057,289
[45] Date of Patent: May 2, 2000

[54] PHARMACEUTICAL COMPOSITION COMPRISING CYCLOSPORIN IN ASSOCIATION WITH A CARRIER IN A SELF-EMULSIFYING DRUG DELIVERY SYSTEM

[75] Inventor: Nirmal Mulye, Long Beach, N.Y.

[73] Assignee: Pharmasolutions, Inc., Cranbury, N.J.

[21] Appl. No.: 09/303,158

[22] Filed: Apr. 30, 1999

[51] Int. Cl.[7] .................................................. A61K 38/00
[52] U.S. Cl. ............................................. 514/11; 514/938
[58] Field of Search ....................................... 514/11, 938

[56] References Cited

U.S. PATENT DOCUMENTS

| | | | |
|---|---|---|---|
| 4,388,307 | 6/1983 | Cavanak | 424/177 |
| 4,874,795 | 10/1989 | Yesair | 514/725 |
| 4,970,076 | 11/1990 | Horrobin | 424/456 |
| 4,990,337 | 2/1991 | Kurihara et al. | 424/427 |
| 4,996,193 | 2/1991 | Hewitt et al. | 514/11 |
| 5,139,997 | 8/1992 | Bach et al. | 503/227 |
| 5,154,930 | 10/1992 | Popescu et al. | 424/489 |
| 5,206,219 | 4/1993 | Desai | 514/3 |
| 5,342,625 | 8/1994 | Hauer et al. | 424/455 |
| 5,391,377 | 2/1995 | Barnwell | 424/463 |
| 5,484,801 | 1/1996 | Al-Razzak et al. | 514/365 |
| 5,597,562 | 1/1997 | Nomura et al. | 424/85.1 |
| 5,603,951 | 2/1997 | Woo | 424/455 |
| 5,639,724 | 6/1997 | Cavanak | 514/11 |
| 5,645,856 | 7/1997 | Lacy et al. | 424/455 |
| 5,650,172 | 7/1997 | Matsuda et al. | 424/489 |
| 5,807,820 | 9/1998 | Elias | 514/11 |
| 5,824,638 | 10/1998 | Burnside et al. | 514/3 |
| 5,858,401 | 1/1999 | Bhalani et al. | 424/450 |
| 5,919,459 | 7/1999 | Nacy et al. | 424/192.1 |
| 5,929,030 | 7/1999 | Hamied et al. | 514/6 |
| 5,962,014 | 10/1999 | Hauer et al. | 424/450 |
| 5,962,017 | 10/1999 | Hauer et al. | 424/450 |

FOREIGN PATENT DOCUMENTS

| | | |
|---|---|---|
| WO 98/40094 | 9/1998 | WIPO . |
| WO 99/20296 | 4/1999 | WIPO . |

*Primary Examiner*—Kimberly Jordan
*Attorney, Agent, or Firm*—Scully, Scott, Murphy & Presser

[57] ABSTRACT

The present invent is directed to a pharmaceutical composition comprising a pharmaceutically effective amount of cyclosporin in association with a pharmaceutical carrier, said carrier comprising a drug solubilizing effective amount of a fatty acid having 6–22 carbon atoms and a non-ionic surfactant.

28 Claims, No Drawings

PHARMACEUTICAL COMPOSITION COMPRISING CYCLOSPORIN IN ASSOCIATION WITH A CARRIER IN A SELF-EMULSIFYING DRUG DELIVERY SYSTEM

FIELD OF THE INVENTION

The present invention relates to a carrier system in a pharmaceutical composition containing cyclosporin.

BACKGROUND OF THE INVENTION

The Cyclosporins comprise a class of structurally distinctive, cyclic, poly-N-Methylated undecapeptides, commonly possessing pharmacological, in particular immunosuppressive, anti-inflammatory and/or anti-parasitic (in particular anti-protozoal, e.g. anti-malarial) activity. The first of the Cyclosporins to be isolated was the naturally occurring fungal metabolite Ciclosporin or Cyclosporine, also known as cyclosporin A and commercially available under the Registered Trademark SANDIMMUN® or SANDIMMUNE®.

Cyclosporin is a highly lipophilic drug. Therefore, cyclosporin is sparingly soluble in water, but dissolves readily in organic solvents, such as methanol, ethanol, chloroform and the like. Due to its limited solubility in water, the bioavailability of orally administered cyclosporin is extremely low. Poor bioavailability may lead to ineffective therapy, the need for higher dosing and/or undesirable side effects. Therefore, it is very difficult tc provide an effective therapeutic concentration of the drug in the body when administered orally or by routes requiring transmembrane absorption. Cyclosporin can only be formulated into a preparation for oral administration only with great difficulty. Accordingly, numerous studies have been extensively conducted to find a cyclosporin preparation effective for oral administration, that is, a preparation which provides both uniform dosage and bioavailability of the active component.

In the prior art preparations of cyclosporin suitable for oral administration, sparingly water-soluble cyclosporin has been usually formulated by combining cyclosporin with a surfactant, an oil and a co-surfactant. For example, U.S. Pat. No. 4,388,307 discloses a liquid formulation of cyclosporin that includes at least one of the following components: (a) a transesterification product of a natural or hydrogenated vegetable oil and a polyalkylene polyol; (b) a saturated fatty acid triglyceride; or (c) a mono- or diglyceride. Component (a) is formed by the transesterification of a triglyceride, e.g., a triglyceride from a vegetable oil, with polyethylene glycol. Component (b) may be obtained by esterifying a triglyceride with saturated fatty acid while component (c) is a mono- or di-glyceride, or a mono- or di-fatty acid glyceride. It is preferred that ethanol be further used as a solubulizing agent. However, since this liquid formulation is administered as an aqueous solution, it is both inconvenient and difficult to administer in an uniform dosage.

In order to mitigate the inconvenience of diluting a cyclosporin liquid composition with water prior to oral administration, the liquid composition was formulated into a soft capsule preparation, which is now commercially available as SANDIMMUN®. In this preparation, the cyclosporin soft capsule contains a large amount of ethanol as a cosurfactant in order to solubilize the cyclosporin. However, since ethanol permeates the gelatin shell of the capsule and is volatile even at normal temperatures, the constitutional ratio of the contents of the soft capsules may greatly vary during storage. The resulting reduced ethanol content may in turn result in crystallization of the cyclosporin and thus results in a significant variation in the bioavailability of cyclosporin. The variation in cyclosporin concentration in this formulation makes it quite difficult to determine the dosage needed to provide a desired therapeutic effect.

Belgian Patent No. 895,724, which relates to the use of Ciclosporin in the treatment of multiple sclerosis, also describes two oral formulations suitable for the administration of this particular compound. Both of these are based on the commercial Ciclosporin (SANDIMMUN®) drinksolution, with adaption to suit the particular cyclosporin active ingredient. The first comprises 5–10% Ciclosporin, 10–12% ethanol, 30–40% MAISINE®, about 4% CREMOPHORE® and 51–30% LABRAFIL®. This corresponds to the composition of the liquid oral formulation of SANDIMMUN®, but with the replacement of the natural vegetable oil component with MAISINE® and the introduction of a minor percentage of the tenside CREMOPHORE®. MAISINE® is a trans-esterification product of corn oil with glycerol. The ratio of Cyclosporin: tenside in the disclosed composition is 1:0.4–0.8. Inasmuch as ethanol is a key component of the formulation, it does not make any suggestion to replace ethanol as co-solvent/cosurfactant.

An Australian Patent Application discloses the use of tensides belonging to the group comprising polyethoxylated castor oils, polyethoxylated hydrogenated castor oils and polyethoxylated fatty acids derived from castor oil or hydrogenated castor oil, such as CREMOPHOR®, MYRJ®, and NIKKOL HCO-60®, as solubilizers for the incorporation of sparingly soluble pharmaceutical agents into controlled release systems such as hydrophillic gel systems. It alleges that ciclosporine is an example of a drug that is difficult to solubilize, although it gives no specific embodiment containing this drug.

U.S. Pat. No. 5,342,625 discloses cyclosporin in association with a hydrophilic phase, lipophilic phase and a surfactant. The hydrophilic phase comprises 1,2-propylene glycol or $R_1$—[O—$CH_2$)$_x$]—$OR_2$, where $R_1$ and $R_2$ are independently alkyl containing 1–5 carbon atoms or tetrahydrofuryl and x is 1–6 and $R_2$ is hydrogen. Such ethers are commercially available under the trade name of Transcutol and Glycofurol; in addition, it may contain $C_{1-5}$ alkanols, such as ethanols.

However, the use of ethanol as well as other solvents such as 1,2,propylene glycol or liquid polyethylene glycols in these sorts of systems creates several problems. Since ethanol permeates the gelatin shell of the capsule and is volatile, even at room temperature, the constitutional ratio of the contents of the soft capsules may greatly vary during storage. The resulting reduced ethanol content may in turn result in crystallization of the cyclosporin, and this results in a significant variation in the bioavailability of cyclosporin when administered to an animal. The variation in cyclosporin concentrate in these types of formulations makes it quite difficult to determine the dosage needed to provide a desired therapeutic effect. Moreover, when solvents such as ethanol, 1,2-propylene glycol and liquid polyethylene glycols are utilized in gelatin capsules, these solvents have a tendency to absorb moisture, thereby rendering brittle the shell walls, especially those in hard gelatin capsules, and thereby resulting in leakage of the contents of the capsules during storage or shipment. Moreover, one of the biggest drawbacks using hydrophilic components, as in U.S. Pat. No. 5,342,625, has beer the potential of reprecipitation of the drug from the formulation when it comes into contact with aqueous systems, such as in the stomach or intestine after ingestion by the mammal.

Moreover, the complexity of the ternary formulations as in U.S. Pat. No. 5,342,625 makes them costly and difficult to manufacture. Moreover, U.S. Pat. No. 5,342,625 suggests the use of solvents such as Glycofurol and Transcutol which are restricted for pharmaceutical use by several regulatory agencies worldwide, including the FDA, because they are not considered "Generally Recognized As Safe" (GRAS) for oral use. Further, with hydrophilic solvents there is always an added risk of precipitation of the cyclosporin on exposure to gastrointestinal fluids in vivo, thereby further affecting bioavailability.

U.S. Pat. No. 4,970,076 discloses use of GLA (gamma linoleic acid) and DGLA (dihomogammalinolenic acid) and their derivatives as active components in pharmaceutical compositions to counter the adverse side effects of cyclosporin, such as nephrotoxicity and renal side effects. It, however, does not teach or even recognize the use of the lipophilic materials for enhancing the solubility, bioavailability, emulsion or microemulsion capability.

A couple of very recent patents, U.S. Pat. Nos. 5,759,997 and 5,858,401, disclose the use of a mixture of mono-, di- and triglycerides and a monoglyceride respectively, as a carrier for cyclosporin formulations. The formulations therein do not contain a hydrophilic component, such as alcohol, propylene glycol, and the like. However, the formulation therein has several drawbacks. For example, some of the problems encountered with these formulations includes the limited solubility of cyclosporin therein. As a result, the size of the capsules required to accommodate the required dose, e.g., 100 mg, is very large. This causes a major inconvenience to the patient, resulting in a larger pill or capsule, thereby making it more difficult for the patient to swallow the same. This in turn, tends to minimize compliance by the patients who have to take multiple capsules per day.

Moreover, in addition, the stability of this formulation, especially those having a high monoglyceride content when used in hard gelatin capsules, is extremely limited; monoglycerides have a tendency to make the gelatin shells brittle, causing leakage of the contents of such capsules.

It is apparent that there is a need to prepare formulations of cyclosporins which minimize the number of components that are to be administered to the patient. There is also a need to prepare formulations of cyclosporin having greater solubility which provide higher drug loading, use components considered as GRAS and offer advantageous formulation stabilities, desirable pharmokinetics and bioavailability and/ or ease of manufacture.

The present inventor has surprisingly found such a system which overcomes the problems of limited solubility and resulting bioavailability associated with cyclosporin. Unlike the formulation used heretofore, it has been found that the use of a carrier system comprising a non-ionic surfactant in conjunction with a cyclosporin solubilizing agent consisting essentially of $C_6$–$C_{22}$ fatty acids overcomes the problems described herein.

No one heretofore utilized the carrier system of the present invention or realized the advantages, as described hereinbelow, of this carrier system in combination with cyclosporin.

It has been found that by employing the above defined carrier system, it is possible to obtain cyclosporin formulations which do not require any solvent or co-solvent such as alcohol, propylene glycol, polyethylene glycol, and the like, in amounts effective to solubilize the drug. Therefore, problems associated with these solvents, as mentioned hereinabove, are eliminated by the present invention. Thus, the compositions of the present invention are more stable and provide higher drug-loading than those compositions containing cyclosporin associated with alcohols, in which the alcohols are utilized and present in amounts effective for dissolving cyclosporin or acting as surfactants or co-surfactants.

Due to the greater solubility of cyclosporin in the $C_1$–$C_{22}$ fatty acids, the present formulation has a concomitant advantage: there is an increase in drug loading. For example, the size of the capsule for the delivery of unit doses containing cyclosporin is reduced in the present invention, providing greater patient acceptance and compliance. Moreover, if the oral dosage form is a capsule, there is an excellent compatibility of the $C_6$–$C_{22}$ fatty acids with hard or soft shell gelatin capsules, thereby preventing brittleness and leakage of the formulation during storage. Furthermore, the present pharmaceutical composition is a preconcentrate which forms an emulsion, preferably forms a fine emulsion and most preferably forms a microemulsion upon exposure to aqueous fluid (e.g., water, for instance the g.i. tract) which provides higher and uniform bioavailability. This characteristic further helps reduce the intra- and inter-subject variability associated with the absorption of the lipophilic active component, as well as minimize the effect of food on the absorption and bioavailability of cyclosporin in mammals.

SUMMARY OF THE INVENTION

The present invention is directed to a pharmaceutically acceptable carrier to be used in association with cyclosporin, said pharmaceutically acceptable carrier preferably having similar lipophilicity to the cyclosporin, thereby providing maximal solubility for the drug. In an embodiment thereof, the present invention encompasses this pharmaceutically acceptable carrier associated with a pharmaceutically effective amount of cyclosporin, said carrier comprising (a) a cyclosporin solubilizing agent consisting essentially of $C_6$–$C_{22}$ fatty acids present in an amount sufficient to solubilize the cyclosporin therein and (b) a water soluble non-ionic surfactant, said surfactant being present in an amount sufficient to form an emulsion, and more preferably a fine emulsion and most preferably a microemulsion when in contact with an aqueous medium, especially the aqueous medium found in mammals. The present invention is also directed to a pharmaceutical composition comprising the carrier described hereinabove and the cyclosporin. Moreover, the present invention is also directed to a method of enhancing the solubility of cyclosporin in a pharmaceutical composition containing same, comprising thoroughly mixing the cyclosporin with a cyclosporin solubilizing agent consisting essentially of fatty acids, containing 6–22 carbon atoms. Moreover, the present invention is directed to a method of forming a pharmaceutical composition containing cyclosporin as the active therapeutic agent capable of forming an emulsion and more preferably a fine emulsion and most preferably a microemulsion when in contact with water or an aqueous system, which method comprises thoroughly mixing the cyclosporin with the carrier as defined herein to form an emulsion, preferably a fine emulsion and most preferably a microemulsion, when in contact with an aqueous medium.

DETAILED DESCRIPTION OF THE INVENTION

As indicated hereinabove, an aspect of the present invention relates to a pharmaceutically acceptable carrier system in association with cyclosporin in a pharmaceutical formulation. It is preferred that the formulation be used in an oral dosage form, e.g., in hard or soft gelatin capsules (or capsules made of other materials such as starch, cellulose or its derivatives, etc.).

Cyclosporin, which is used as the pharmaceutically active ingredient in the composition according to the present invention, is a cyclic peptide compound having useful immunosuppressive activity and anti-inflammatory activity. Although various cyclosporins, such as cyclosporin A, B, C, D, G and the like can all be used as the cyclosporin component in the present invention, cyclosporin A is preferred. It is present in the composition of the present invention in pharmaceutically effective amounts. These amounts are well-known in the art. For example, when treating chronic inflammations or provoking an immunosuppressive effect, it is preferred that the daily dose ranges from about 3 mg/kg to about 50 mg/kg. in a preferred embodiment the cyclosporin is present in amounts ranging from about 5 to about 35% by weight of the pharmaceutical composition.

As defined by the present invention, cyclosporin is associated with a carrier system comprising a non-ionic surfactant and a cyclosporin solubilizing agent consisting essentially of a free fatty acid.

An essential component of the pharmaceutical carrier of the present invention, as indicated hereinabove, is the cyclosporin solubilizing agent, i.e., an agent that solubilizes the cyclosporin in the pharmaceutical carrier associated therewith. It consists essentially of free fatty acids. The fatty acid is the component that is substantially responsible for the solubilization of cyclosporin in the carrier associated therewith. It may contain other components normally used in the pharmaceutical arts, such as diluents. Preferably, these other components do not have the ability to solubilize cyclosporin. It is preferred that at least about 20% by weight and even more preferred that at least about 50% by weight and especially preferred that at least 75% by weight and more especially preferred that at least 90% by weight of the cyclosporin solubilizing agent is free fatty acid. It is more preferred that the cyclosporin solubilizing agent is comprised substantially of free fatty acids. It is most preferred that the only component cf the cyclosporin solubilizing agent is the free fatty acid.

The free fatty acids, as defined herein, are organic acids having 6–22 carbon atoms. More specifically, the free fatty acid as defined by the formula R COOH or pharmaceutically acceptable salts thereof, wherein R is a hydrocarbyl group containing only carbon and hydrogen atoms containing 5–21 carbon atoms. The fatty acids may be straight chain or branched. The R group may be completely saturated or may contain at least one carbon-carbon double bond. It is preferred that the R group is an alkyl or alkenyl group. It is more preferred that this R group is saturated or contains 1, 2, 3 or 4 carbon-carbon double bonds. It is even more preferred that the R group is saturated or contains 1 or 2 carbon-carbon double bonds.

Moreover, it is most preferred that the fatty acids utilized in the present invention are regarded as Generally Recognized As Safe (GRAS) by the FDA for oral use. The more preferred fatty acid contain 12–18 carbon atoms. The most preferred fatty acid is oleic acid.

Although a mixture of fatty acids of $C_6$–$C_{22}$ may be used, it is preferred that only one type of fatty acid be used, based on the lipophilicity, the solubility, and/or stability of the drug. Further, based on the intended dosage form such as soft gelatin or hard gelatin capsules, one may judiciously combine the individual fatty acids for optimum solubility of the drug and compatibility with the shells used such as soft or hard gelatin capsules or non-gelatin capsules.

The free fatty acids used in the present invention are commercially available or are prepared by art-recognized techniques. Commercially available fatty acids may be subjected to purification and/or refinement before being utilized in the present formulation.

In the composition of the present invention, it is preferred that the cyclosporin solubilizing agent is present in amounts sufficient to solubilize cyclosporin. It is preferred that the weight ratio of cyclosporin to fatty acids described hereinabove ranges from about 1:0.4 to about 1:20, and more preferably ranges from about 1:2 to about 1:4. Most preferably, the cyclosporin and fatty acids are present in a weight ratio of about 1:2, respectively.

As indicated hereinabove, the present carrier system solubilizes cyclosporin.

It is preferred that the lipophilicity of the fatty acid in the cyclosporin solubilizing agent is similar to that of cyclosporin. As used herein, lipophilicity is a term of art. Lipophilic molecules, as defined herein, are those having a partition coefficient (log p) in octanol/water, n-octanol/butter or n-octanol/saline greater than 1. In other words, it is preferred that the octanol/saline partition coefficient of the fatty acid be similar, e.g. be within about 2 units (±2 units), relative to that c)f the cyclosporin used in the present formulation.

The present inventor has found that the fatty acid, when used in the amounts indicated hereinabove, surprisingly enhances the solubility of cyclosporin. As a result, the pharmaceutical composition, when combined with an effective amount of the non-ionic surfactant, in accordance with the present invention, provides a self emulsifying drug delivery system (SEDDS) which exhibits excellent bioavailability of the cyclosporin in vivo. In addition, the present formulation also exhibits greater stability.

For example, the solubilization of cyclosporin in a composition containing free fatty acids, such as oleic acid, was found to be superior compared to any formulations containing hydrophobic and/or lipophilic materials without the free fatty acids. For example, unlike the composition of the present invention, formulations containing no free fatty acid exhibited crystallizaion when stored at room or lower temperatures, within a few days, and so these formulations are not suitable for such products in oral or parenteral pharmaceuticals. The compositions of the present invention containing free fatty acids of $C_6$–$C_{22}$ in the carrier did not exhibit crystallization of cyclosporin under the same storage conditions.

More specifically, cyclosporin is extremely soluble in the composition of the present invention. The present formulation does not require the presence of ethanol, which is typically used for purposes of solubilizing cyclosporin for purposes of administration, as in the prior art formulations.

Another essential component of the carrier system in the pharmaceutical composition of the present invention is the water soluble non-ionic surfactant. It is preferred that the surfactant haze a HLB (Hydrophilic Lipophilic Balance) greater than 10, more preferably greater than 12 and most preferably greater than 14. The surfactant is capable of forming a stable emulsion, for example, preferably a fine emulsion and more preferably a microemulsion, of the present composition when it is brought into contact with aqueous fluid, such as in the G.I. tract. Examples of the preferred surfactants according to the present invention include polyoxyethylene products of hydrogenated vegetable oils, polyethoxylated castor oils or polyethoxylated hydrogenated castor oil, polyoxyethylene-sorbitan-fatty acid esters, polyoxyethylene castor oil derivatives and the like, for example, NIKKOL HCO-50®, NIKKOL HCO-35®, NIKKOL HCO-40®, NIKKOL HCO-60® (from Nikko Chemicals Co. Ltd.); CREMOPHORE® (from BASF) such as CREMOPHORE RH40®, CREMOPHORE RH60®, CREMOPHORE EL®, TWEENS (from ICI Chemicals) e.g., TWEEN 20®, TWEEN 21®, TWEEN 40®, TWEEN 60®, TWEEN 80®, TWEEN 81®, CREMOPHORE RH 410®, CREMOPHORE RH 455® and the like.

The surfactant can include more than one non-ionic surfactant, as defined hereinabove, including any of the above-mentioned surfactants alone or in combination with one or more surfactants. In the composition according to the present invention, it is preferred that the fatty acid and surfactant be used in a weight ratio ranging from about 1:0.1 to about 1:20, respectively, and more preferably ir the range of about 1:1 to about 1:4 and most preferably about 1:1.5 to about 1:2.

In the pharmaceutical composition of the present invention the three essential components, i.e., the cyclosporin, the cyclosporin solubilizing agent, e.g. fatty acid and the non-ionic surfactant, as defined herein, are present preferably in the weight ratio of cyclosporin, fatty acid and surfactant ranging from about 1:0.4–20:0.1–20, respectively and even more preferably from 1:2–4:2–6 and most preferably about 1:2:3. If the cyclosporin solubilizing agent contains components other than the fatty acids, the solubilizing agent including the fatty acid is preferably present in amounts ranging from about 5% to about 99% by weight of the pharmaceutical composition.

Additives and diluents normally utilized in the pharmaceutical arts can optionally be added to the pharmaceutical composition and especially the carrier. These include thickening, granulating, dispersing, flavoring, sweetening, coloring, and stabilizing agents, including pH stabilizers, other excipients, anti-oxidants (e.g., tocopherol, BHA, BHT, TBHQ, tocopherol acetate, ascorbyl palmitate, ascorbic acid propyl gallate, and the like), preservatives (e.g., parabens), and the like.

It is preferred that an anti-oxidant is present in the pharmaceutical composition of the present invention. If the fatty acid contains carbon-carbon double bonds, they may be prone to oxidation; therefore, if the anti-oxidant is present, it is present in anti-oxidizing effective amounts, i.e., amounts effective to prevent oxidation of the fatty acids and more specifically, the double bonds that are present thereon. It is preferred that the antioxidant is present in at least about 0.1% by weight of the pharmaceutical composition, and more preferably from about 0.1% to about 2% by weight of the pharmaceutical.

The present pharmaceutical composition is prepared by uniformly and thoroughly mixing the fatty acid, cyclosporin, and the surfactant together at room temperature or at slightly elevated temperature, such as temperatures up to about 60° C. until a clear solution is obtained, and then cooled to room temperature. The other additives indicated hereinabove are then thoroughly admixed therewith. The cyclosporin remains in solution and does not crystallize or precipitate out.

An essential aspect of the pharmaceutical formulation of the present invention is that it forms an emulsion, e.g., a fine emulsion and preferably a microemulsion, when placed in contact with water or an aqueous medium. The emulsion, e.g., fine emulsion or microemulsion, thus formed is thermodynamically stable when it comes into contact with the water or aqueous medium, as in the G.I. fluids of mammals. However, until the present formulation comes in contact with an aqueous medium, it is not an emulsion; instead, when the various components are mixed, it forms a preconcentrate of an emulsion (SEDDS), e.g., fine emulsion pre-concentrate or microemulsion pre-concentrate, i.e., a system capable of forming an emulsion, e.g., fine emulsion or microemulsion respectively, on contact with water or aqueous system.

If a microemulsion is formed when it comes in contact with an aqueous system, it consists of substantially uniform and spherical droplets dispersed in a continuous medium. It is substantially non-opaque, i.e., is transparent or opalescent. The particle size of the droplets in the present microemulsion are less than about 200 nm, which explains the optical transparency. In a preferred embodiment, the average particle size is less than about 40 nm and more preferably less than about 20 nm. In an even more preferred embodiment, substantially all of the particles are less than about 40 nm and more preferably less than about 20 nm.

Thus, the microemulsions formed in the present invention when brought into contact with aqueous medium are ideal for oral delivery systems, since they are homogeneous, thermodynamically stable, have uniform droplet sizes of approximately 20–40 nanometers and are optically clear. A fine emulsion, on the other hand, has larger droplet sizes, preferably less than 50 μm and more preferably, about 0.1 μm to 15 μm.

By forming this emulsion when in contact with aqueous medium, the present formulation minimizes and especially eliminates the risk that the cyclosporin will precipitate or crystallize out of the aqueous dispersion, i.e., the emulsion. In addition, it enhances the absorption of the cyclosporin into the mammal.

Thus, the present formulation not only increases the solubility of the cyclosporin in the pharmaceutical carrier but also enhances the solubility thereof in the treated mammal and facilitates uniform absorption thereof in the treated mammal.

In addition, the microemulsion and/or emulsion formed by the carrier system of the present formulation in contact with water gives faster onset of action.

Compositions of the present invention are preferably administered to mammals, such as dog, cat, horse, pig, mice, rat and especially humans. It is preferred that the pharmaceutical compositions of the present invention are administered orally in capsule, tablet, liquid-oral, powder, or the like or liquid for parental composition for intramuscular or intravenous administration. In a preferred embodiment, the invention provides a composition in a form appropriate or adapted for oral administration, in particular, in oral unit dosage form, e.g., in the form of tablets, capsules, drink solutions or dry powder for reconstituting; or a sohxlet form prepared by standard techniques known in the art, such as by spray coating on deposition. Especially suitable unit dosage forms for oral administration include encapsulated forms, e.g., soft or hard gelatin encapsulated forms, which is the preferred oral dosage form.

Oral unit dosage forms in accordance with the present invention will suitably comprise from 5 to 400 mg and more preferably from 20 to 200 mg, e.g., 25, 50, 100, 125, 150, or 200 mg of cyclosporin. The dosage of the drug and the number of times administered to the patient will vary depending on several factors, the age of the patient, the severity of the condition of the patient, past medical history, among other factors, and will be determined by the physician in his sound discretion.

When the composition of the present invention is prepared in the form of a soft or hard capsule, the composition may be encapsulated in a gelatin shell which contains any conventional plasticizer. As the plasticizer which can be included in the gelatin capsule shell, one or more selected from the group consisting of glycerine, sorbitol, hexanetriol propylene carbonate, hexane glycol, sorbitans, tetrahydrofuryl alcohol ether, diethylene glycol monoethyl ether, 1,3-trimethyl-2-imidazolidone, dimethylisosorbide, etc. can be used without any limitation. However, it should be understood that the plasticizer which can be used in the present invention is not restricted to those mentioned above.

Capsule preparation according to the present invention can be prepared in a conventional machine by encapsulating the resulting preconcentrates of the emulsion of the present invention, e.g., the microemulsion pre-concentrate with or without the above-mentioned pharmaceutically acceptable additives.

Since ethanol is preferably not present, especially in amounts sufficient to solubilize the cyclosporin, there is less risk of precipitating or crystallizing the cyclosporin in the pharmaceutical composition. If ethanol were present, and if it were present in the amounts usually found in cyclosporin formulations described in the prior art, it would evaporate even when standing at room temperature, thereby causing possible crystallization and/or precipitation of the cyclosporin. The absence of ethanol in these amounts in the present formulation prevents possible crystallization and precipitation of the cyclosporin, thereby ensuring dosage uniformity, accurate blood levels of cyclosporin and consistent therapeutic performance.

Moreover, there is no need for special precaution and procedure for the manufacturing, packaging and handling requirement during the preparation, storage and shipping of the product since ethanol is not present.

Due to the greater solubility of the drugs in the $C_6$–$C_{22}$ fatty acids, the size of the capsule for the delivery of unit doses of the lipophilic drug is reduced, providing greater patient acceptance and compliance. Moreover, if the oral dosage form is a capsule, there is an excellent compatibility of the $C_1$–$C_{22}$ fatty acids with hard or soft shell gelatin capsules, thereby preventing brittleness and leakage of the formulation during storage. Furthermore, the present pharmaceutical composition is a preconcentrate (SEDDS) which forms an emulsion and preferably fine emulsion and more preferably forms a microemulsion upon exposure to aqueous fluid (water, in e.g., the g.i. tract) which provides higher and uniform bioavailability. This characteristic further helps reduce the intra- and inter-subject variability associated with the absorption of the lipophilic active component, as well as minimize the effect of food on the absorption and bioavailability of cyclosporin in mammals.

In addition, the compositions of the invention exhibit improved stability on storage as compared with compositions based on the use of ethanol or equivalent alkanols and are, in particular, better adapted, e.g., for presentation in capsule, e.g. hard or soft gelatin capsule form. Compositions in accordance with the present invention which are free or substantially free of ethanol have the particular advantage of eliminating or substantially reducing packaging difficulties, e.g. in relation to the packaging of soft gelatin encapsulated forms.

The present pharmaceutical forms a more stable system and is capable of holding a larger amount of cyclosporin than prior art formulations.

Moreover, the present formulation can also be administered as a parenteral preparation for intra-muscular or even intravenous use.

Thus the present pharmaceutical formulation has several advantages. It exhibits (I) an enhanced solubility of cyclosporin, thereby providing for higher drug loading and reducing the size of oral unit dosage of same (e.g., the size of the capsule will be reduced); (II) greater and uniform bioavailability; (III) better storage stability; (IV) reduced inter and intra-subject variability, and (V) minimal effect of food on the oral absorption of the drug. Moreover the present formulation utilizes GRAS material for oral use. Furthermore, administration of the present formulation in the reduced size dosage forms, such as capsules will facilitate greater patient acceptance and compliance. Administration of the present formulation in the reduced size dosage forms, such as capsules, will facilitate greater patient acceptance and compliance.

As used herein, the term a "drug" refers to "cyclosporin", thus, the two terms are used interchangeably without changing the meaning thereof.

Moreover, the term "aqueous medium" as used herein, includes water, fluids containing water and in vivo media in mammals, such as the a(aqueous fluid present in the G.I. tract thereof.

Unless indicated to the contrary the % utilized are in weight percentages.

The chemical composition of the trademarked chemicals are described in U.S. Pat. No. 5,639,724, the contents of which are incorporated by reference.

The following examples further illustrate the present invention.

EXAMPLE 1

| Ingredient | mg |
| --- | --- |
| Cyclosporin | 100 |
| Oleic Acid | 200 |
| Polyoxyl 35 Castor Oil | 300 |
| TOTAL | 600 |

This example utilized the above ingredients in the amounts indicated. The cyclosporin was dissolved in the oleic acid and was thoroughly mixed at room temperature until the drug was dissolved. The polyoxyl castor oil was added and then mixed therewith for a few minutes at room temperature until the solution was homogenous.

The solution was then stored overnight up to 24 hours to ensure that no crystallization occurred.

To verify that an emulsion was formed, 1 part of the formulation was added to 10 parts of water and stirred gently. The drug did not precipitate or crystallize and it formed a fine emulsion.

The formulation is ready for encapsulation into a capsule.

EXAMPLE 2

The procedure of Example 1 is followed except the formulation contains the following:

| Ingredient | mg |
|---|---|
| Cyclosporin | 25 |
| Oleic Acid | 100 |
| Polyoxyethylene sorbitan ester | 300 |
| TOTAL | 425 |

EXAMPLE 3

The procedure of Example 1 is followed, except the formulation contains the following:

| Ingredient | mg |
|---|---|
| Cyclosporin | 25 |
| Oleic Acid | 100 |
| Polyoxyl 40 Hydrogenated Castor Oil | 300 |
| TOTAL | 425 |

EXAMPLE 4

The procedure of Example 1 is followed except the formulation contains the following:

| Ingredient | mg |
|---|---|
| Cyclosporin | 100 |
| Oleic Acid | 200 |
| Polyoxyl 35 Caster Oil | 400 |
| TOTAL | 700 |

COMPARATIVE EXAMPLES 1–3

To show the improved solubility of the cyclosporin in the pharmaceutical composition of the present invention, the formulation of the present invention (Example 1) was compared with formulations in which all of the components were the same except component (b). The component (b) used in Comparative Examples 1–3 are components normally found in pharmaceutical compositions for enhancing solubility of the cyclosporin. The solubility of the drug formulations (Comparative Examples 1–3) was compared with that of the pharmaceutical formulation of the present invention. (Example 1).

The formulations were prepared by mixing the components described hereinbelow at room temperature until a clear solution was formed. The resulting formulations were stored for 4 weeks and then compared. The results are tabulated hereinbelow:

| | Components | Weight in mg | Observations (initial) | Storage at Room Temp. for 4 Weeks |
|---|---|---|---|---|
| Comp. Ex. 1 | a. Cyclosporin<br>b. Miglycol - 812[1]<br>c. Cremophore[2] | 100<br>200<br>300 | Clear | Crystal or precipitation |
| Comp. Ex. 2 | a. Cyclosporin<br>b. Imwitor 742[3]<br>c. Cremophore | 100<br>200<br>300 | Clear | Precipitate |

[1]Miglycol 812 is a medium chain triglyceride.
[2]Cremophore is polyoxyl 35 castor oil.
[3]Imwitor 742 is a mixture of mono- and diglycerides, viz., glyceryl mono-, di-caprylate/caprate.

| | Components | Weight in mg | Observations (initial) | Storage at Room Temp. for 4 Weeks |
|---|---|---|---|---|
| Comp. Ex. 3 | a. Cyclosporin<br>b. Capmul MCM[4]<br>c. Cremophore | 100<br>200<br>300 | Clear | Precipitate |
| Ex. 1 | a. Cyclosporin<br>b. Oleic Acid<br>c. Cremophore | 100<br>200<br>300 | Clear | Clear |

[4]Capmul MCM is glycerol caprylate/caprate containing more than 50% monoglycerides.

As clearly shown by the data, in the present formulation, the cyclosporin did not crystallize or precipitate out. On the other hand, cyclosporin in the comparative examples crystallized out of solution. Thus, the present formulation is more suitable for use in pharmaceutical formulations for it enhances the ability of the cyclosporin to remain solubilized and provides enhanced drug loading.

The above preferred embodiments and examples are given to illustrate the scope and spirit of the present invention. These embodiments and examples will make apparent to those skilled in the art other embodiments and examples. These other embodiments and examples are within the contemplation of the present invention.

Therefore, the present invention should be limited only by the appended claims.

What is claimed is:

1. A pharmaceutical composition comprising a pharmaceutically effective amount of cyclosporin in association with a pharmaceutical carrier, said carrier comprising (a) a cyclosporin solubilizing agent consisting essentially of a solubilizing effective amount of a fatty acid of $C_6$–$C_{22}$ carbon atoms, and (b) a non-ionic surfactant having an HLB value greater than 10, said non-ionic surfactant being present with the cyclosporin solubilizing agent and cyclosporin in an amount sufficient to form an emulsion when brought into contact with an aqueous medium in a mammal.

2. The pharmaceutical composition according to claim 1 wherein said emulsion is a fine emulsion.

3. The pharmaceutical composition according to claim 1 wherein the emulsion is a microemulsion.

4. The pharmaceutical composition according to claim 1 wherein the surfactant is polyoxyethylene sorbitan ester, the polyethoxylated product of hydrogenated vegetable oils, polyethoxylated castor oil, polyethoxylated hydrogenated castor oil, polyoxyl 35 castor oil or polyoxyl 40 hydrogenated castor oil.

5. The pharmaceutical composition according to claim 1 wherein cyclosporin, fatty acid and nonionic surfactant are present in a weight ratio ranging from about 1:0.4–20:0.1–20, respectively.

6. The pharmaceutical composition according to claim 5 wherein the weight ratio ranges from about 1:2–4:2–6.

7. The pharmaceutical composition according to claim 6 wherein the weight ratio is 1:2:3.

8. The pharmaceutical composition according to claim 1 wherein the weight ratio of cyclosporin to fatty acid ranges from about 1:0.4 to about 1:20.

9. The pharmaceutical composition according to claim 8 wherein the weight ratio of cyclosporin to fatty acid ranges from about 1:2 to about 1:4.

10. The pharmaceutical composition according to claim 1 wherein the fatty acid contains 12–18 carbon atoms.

11. The pharmaceutical composition according to claim 1 wherein the fatty acid is oleic acid.

12. The pharmaceutical composition according to claim 1 wherein the weight ratio of fatty acid to surfactant ranges from about 1:0.1 to about 1:20.

13. The pharmaceutical composition according to claim 12 wherein the weight ratio of fatty acid to surfactant ranges from about 1:1 to about 1:4.

14. The pharmaceutical composition according to claim 13 wherein the ratio of fatty acid to surfactant is about 1:1.5 to about 1:2.

15. The pharmaceutical composition according to claim 1 wherein the surfactant has an HLB value greater than 12.

16. The pharmaceutical composition according to claim 1 wherein an anti-oxidant is additionally present.

17. The pharmaceutical composition according to claim 16 wherein the anti-oxidant is present in at least 0.1% by weight.

18. A microemulsion or fine emulsion of the pharmaceutical composition according to claim 1 formed when said pharmaceutical composition is brought into contact with an aqueous medium.

19. The pharmaceutical composition according to claim 1 which is in oral dosage unit form.

20. The pharmaceutical composition according to claim 19 wherein the oral dosage unit form is a capsule.

21. The pharmaceutical composition according to claim 1 which is in a liquid oral dosage form.

22. The pharmaceutical composition according to claim 1 which is in a parenteral dosage form.

23. An aqueous dispersion containing the pharmaceutical composition of claim 1.

24. A method of increasing the solubility of cyclosporin in a pharmaceutical composition, said method comprising thoroughly mixing cyclosporin with a cyclosporin solubilizing agent consisting essentially of a solubilizing effective amount of a fatty acid containing 6–22 carbon atoms.

25. A method of forming a self emulsifying drug delivery system of cyclosporin in a pharmaceutical composition, said method comprising (a) thoroughly mixing cyclosporin with (i) a cyclosporin solubilizing agent consisting essentially of a solubilizing effective amount of a fatty acid containing 6–22 carbons; and (ii) a non-ionic surfactant having a HLB value greater than 10, said surfactant being present in sufficient amount to form an emulsion with cyclosporin and said cyclosporin solubilizing agent when in contact with an aqueous medium in a mammal, and (b) administering the product of (a) to a mammal.

26. The method according to claim 25 wherein the emulsion is a microemulsion or a fine emulsion.

27. A method of increasing the drug loading ability of cyclosporin in a pharmaceutical composition, said method comprising thoroughly mixing cyclosporin with (a) a cyclosporin solubilizing agent consisting essentially of a solubilizing effective amount of a fatty acid containing 6–22 carbons and (b) a non-ionic surfactant having a HLB value greater than 10, said surfactant being present in amounts sufficient to form an emulsion with cyclosporin and said cyclosporin solubilizing agent when in contact with an aqueous medium.

28. The method according to claim 27 wherein the emulsion is a fine emulsion or microemulsion.

* * * * *